United States Patent [19]

Emmert

[11] Patent Number: 4,721,874
[45] Date of Patent: Jan. 26, 1988

[54] APPARATUS AND METHOD FOR DETERMINING THE VISCOSITY OF A FLUID SAMPLE

[76] Inventor: Sans W. Emmert, 3057 Ship Rock Rd., Willow Street, Pa. 17584

[21] Appl. No.: 916,784

[22] Filed: Oct. 6, 1986

[51] Int. Cl.⁴ .......................................... H01L 41/08
[52] U.S. Cl. ...................................... 310/333; 73/54; 310/316; 310/324; 310/321
[58] Field of Search ....................... 310/316, 321–324, 310/333–337, 311, 312; 73/54, 59

[56] References Cited

U.S. PATENT DOCUMENTS

| | | | |
|---|---|---|---|
| 2,490,452 | 12/1949 | Mason | 73/54 X |
| 2,518,348 | 8/1950 | Mason | 310/333 X |
| 2,607,216 | 8/1952 | Mason | 310/333 X |
| 3,045,491 | 7/1962 | Hart | 310/333 X |
| 3,302,044 | 1/1967 | Lynnworth et al. | 310/333 |
| 3,903,732 | 9/1975 | Rork et al. | 73/54 |
| 3,943,753 | 3/1976 | Simon | 73/54 |
| 3,948,089 | 4/1976 | Shaw et al. | 310/333 X |
| 4,088,907 | 5/1978 | Jones et al. | 310/333 |
| 4,117,716 | 10/1978 | Simon | 73/54 X |
| 4,565,942 | 1/1986 | Saki et al. | 310/320 X |

FOREIGN PATENT DOCUMENTS 2363236  7/1974  Fed. Rep. of Germany ......... 73/54

OTHER PUBLICATIONS

Piezoelectric Method of Determining Viscosity @ 40 kHz, by W. H. Robinson, J. Appl. Phys., vol. 49, No. 3, Mar. 1978, pp. 1070–1075.
B. Carlin, "Ultrasonics", 2nd Ed., McGraw-Hill, 1960, p. 86.
W. P. Mason et al., "Measurement of Shear Elasticity and Viscosity of Liquids at Ultrasonic Frequencies", Physical Review, vol. 75, No. 6, Mar. 1949, pp. 936–945.
W. Roth et al., "A New Method for Continuous Viscosity Measurement, General Theory of the Ultra-Viscoson", Journal of Applied Physics, vol. 24, No. 7, Jul. 1953, pp. 940–950.
Bulletin 56, of Nametre Company (3 pages), Nov. 1983.
E. Shalis, "Ultrasonic Shear Viscometer for Liquid Droplets and its Applications" (Abstract of doctoral thesis), Apr. 1977.

*Primary Examiner*—Mark O. Budd
*Attorney, Agent, or Firm*—Howson and Howson

[57] ABSTRACT

Viscosity of small fluid samples is measured by coupling an ultrasonically energized shear transducer to a fluid sample through a polymeric coupling layer having a thickness and shear impedance such as to produce a zero total reflection coefficient at least at one particular viscosity. In general, the thickness will be slightly greater than one-quarter wavelength. The use of the coupling layer produces a large increase in sensitivity, eliminates the need for sophisticated and expensive electronic circuitry, and makes it possible to determine viscosity by very simple circuitry responsive to transducer current.

8 Claims, 4 Drawing Figures

APPARATUS AND METHOD FOR DETERMINING THE VISCOSITY OF A FLUID SAMPLE

BRIEF SUMMARY OF THE INVENTION

This invention relates to viscosity measurement, and particularly to a simple and inexpensive apparatus and method for determining the viscosities of fluids using ultrasonic techniques.

Three basic methods have been used in the past for measuring viscosities of fluids using ultrasonic waves. They are the magnetostriction technique, the torsional quartz crystal technique, and the pulse reflectance technique.

With the magnetostriction technique, a magnetostrictive blade is partially immersed in a fluid sample. The viscosity of the sample is ascertained by measurement of the damping constant of a travelling elastic wave in the blade.

The torsional crystal method is carried out by measuring the damping effect produced by a fluid on a torsionally oscillating piezoelectric crystal in the form of a cylinder.

Both the magnetostrictive and torsional crystal techniques utilize comparatively low ultrasonic frequencies. For measurements in the megahertz frequency range, the pulse reflectance technique is used. A piezoelectric shear crystal is bonded to a fused quartz delay rod. The crystal is excited by a pulse of alternating current at a frequency near the mechanical resonant frequency of the transducer. The resulting pulse of shear vibration propagates through the delay rod and is reflected by a fluid sample, which is placed on a polished surface at the opposite end of the delay rod. The reflected pulse is received by the crystal. The viscoelastic properties of the fluid sample are ascertained by measurements of the phase and amplitude of the reflected pulse.

There are various problems in the use of the above-described techniques. With the magnetostrictive and torsional crystal techniques, relatively high sample volumes are required. Complex instrumentation is also necessary because the transducers used in practicing these techniques are not highly sensitive to changes in viscosity. The pulse reflectance technique is applicable to smaller sample volumes. However, even with pulse reflectance, complex instrumentation is required to measure the phase and amplitude of the reflected pulse because, over a wide range of viscosities, the reflection coefficient and phase shift change only by very small amounts. Very sophisticated and expensive electronic equipment is needed to detect these changes and to translate them into indications of viscosity. The high cost of quartz delay rods also contributes to the expense of equipment for carrying out viscosity measurements using pulse reflectance. Temperature control is also critical where the pulse reflectance technique is used, because the velocity of shear waves in fused quartz is dependent on temperature.

Other ultrasonic viscosity measurement techniques have been attempted, but all are believed to have required complex electronic instrumentation to compensate for low transducer sensitivity.

Another problem associated with previous techniques is the problem of mounting the transducer. The physical mounting of a low sensitivity transducer is critical, as even a slight damping of the transducer vibration by the mounting can overwhelm the damping caused by the fluid sample.

I have discovered that the requirements for sophisticated and expensive instrumentation in pulse reflectance measurements can be eliminated by the use of a coupling layer of appropriate thickness. The delay rod can be eliminated altogether, and the coupling layer placed between the transducer and a small fluid sample. The transducer can be energized continuously by a high frequency alternating current, and measurement of the current in the transducer can be used to provide an indication of the viscosity of the sample. The coupling layer is preferably slightly thicker than one-quarter wavelength at the generator frequency and at the velocity of travel of shear waves through the coupling layer. When the thickness of the coupling layer is appropriately chosen, there is at least one viscosity for which the total reflection coefficient is substantially zero. When the coupling layer is of appropriate thickness to produce a zero reflection coefficient at a particular viscosity, then over a very wide range of sample viscosities on both sides of this particular viscosity, the instrument is highly sensitive to changes in viscosity. These viscosity changes are manifested as changes in current in the transducer, which can be easily translated into viscosity indications using simple electronic circuitry.

Specifically, the apparatus in accordance with the invention comprises an electromechanical transducer having a face capable of vibrating in a shear mode when excited by an alternating electrical current. The current is provided by a generating means connected to the transducer. This generating means provides an alternating current at a predetermined frequency, and excites the transducer into shear vibration. A solid coupling layer of substantially uniform thickness has one face in contact with the face of the transducer, and has its opposite face free to come into contact with a fluid sample. Preferably, the coupling layer is horizontal, and the transducer is located underneath the coupling layer, so that the fluid sample can be placed on top of the coupling layer. The apparatus includes means, connected to the current generating means, for measuring the magnitude of the impedance of the system consisting of the transducer, the coupling layer, and the fluid sample. The impedance which is measured is the impedance as presented to the alternating current generator. The thickness of the coupling layer is chosen so that at least at one viscosity of a fluid sample in contact with the face of the coupling layer remote from the transducer, and at the frequency of the alternating electrical current, the magnitude of the shear wave reflected into the transducer through the interface between the coupling layer and the transducer is substantially zero.

The invention has utility in clinical measurements, in cervical mucus viscosity measurements for fertility detection and birth control, in food processing, in petroleum processing, and in various chemical industries and scientific laboratories.

The principal object of this invention is to provide a very simple and inexpensive viscosity measuring instrumennt, the sensitivity and accuracy of which are comparable to the sensitivity and accuracy of much more expensive and cumbersome instruments used in the past. It is also an object of the invention to provide a simple, inexpensive, sensitive and accurate viscosity measuring instrument capable of determining viscosities of very small fluid samples.

Other objects and advantages of the invention will be apparent from the following detailed description when read in conjunction with the drawings.

DETAILED DESCRIPTION

Figure 1:
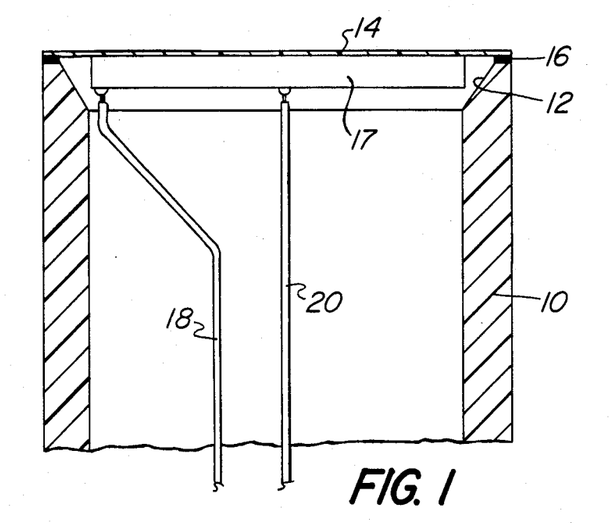
FIG. 1 is an axial section through the upper end of a tubular support having a transducer and coupling layer supported at its end opening.

A preferred form of viscometer in accordance with the invention comprises, as shown in FIG. 1, a tube 10 having an internal bevel 12 at one end. A thin sheet 14 of synthetic polymer, which serves as a coupling layer, is cemented to a face of a shear transducer 17 by a cyanoacrylate adhesive. The thin sheet, with the transducer cemented to it, is placed across the bevelled opening of the tube, and secured to the edge of the tube at the top of the bevel by a thin layer 16 of adhesive. The transducer is electrically energized through flexible leads 18 and 20.

The dimensions and materials of the structure of FIG. 1 can vary considerably. In a typical unit, tube 10 is an acrylic polymer (methyl nethacrylate) having an external diameter of ⅜ inch, and an internal diameter of ¼ inch. It can be of any desired length. Transducer 17 is approximately ¼ inch in diameter. Polymeric sheet 14 is typically a sheet of polyester (poly(ethylene teraphalate)), 0.004 inch thick. The cyanoacrylate adhesive is approximately 0.0007 inch thick. A typical transducer is a PZT-5A piezoelectric ceramic thickness shear transducer, available from Vernitron Corporation, in Bedford, Ohio.

In operation, the device of FIG. 1 is positioned so that the outer face of polyester sheet 14 is horizontal. A small sample of fluid to be tested is placed on the face of the sheet, preferably covering most of the surface of the sheet, if not the entire surface. The thickness of the fluid sample is not critical, and variations in the sample thickness make very little difference in the viscosity measurements delivered by the apparatus. The sample can be of very small size, and need not overlie the entire area of the face of the transducer. However, for repeatability the same area must be covered for each measurement. Therefore, either the entire area of sheet 14 should be covered, or a reduced area should be marked off.

Figure 2:
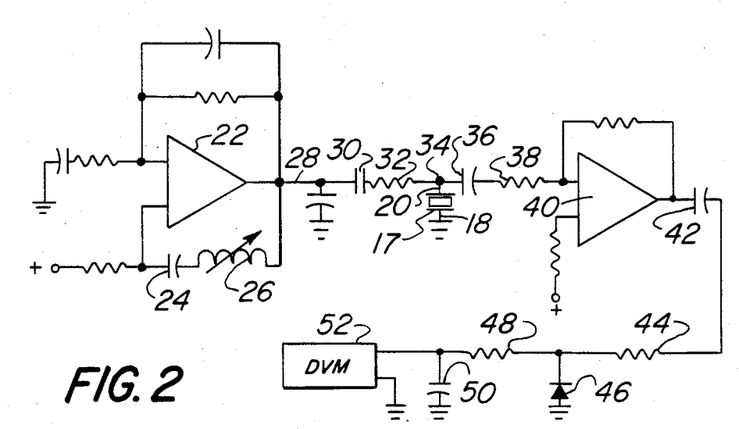
FIG. 2 is an electrical schematic showing the excitation and current measuring circuitry associated with the transducer of FIG. 1.

The circuitry of FIG. 2 energizes the transducer of FIG. 1, and provides an indirect measure of the acoustic impedance of the mechanical system comprising transducer 17, polyester sheet 14, and the fluid sample resting on the polyester sheet.

Amplifier 22 is a current mode differencing input amplifier, preferably one of the two amplifiers packaged as a unit available as No. LM359 from National Semiconductor. It is connected to serve as a high frequency oscillator, there being a capacitor 24, and an adjustable inductor 26 connected in series between its output and one of its two inputs. The output of the oscillator circuit, at line 28, is connected through capacitor 30 and resistor 32 to node 34. Piezoelectric transducer 17, shown schematically in FIG. 2 is connected between node 34 and ground by means of leads 20 and 18. The frequency of the oscillator is preferably chosen to correspond to the natural parallel resonance frequency of the transducer-coupling layer combination. It is typically about 1.98 MHz.

Figure 3:
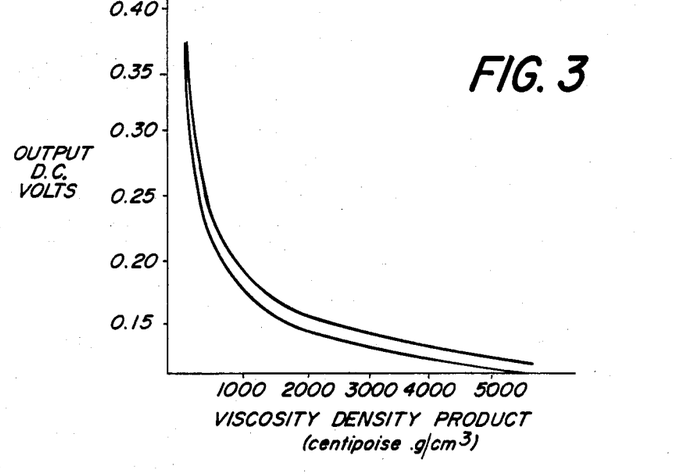
FIGS. 3 and 4 are rectangular graphs in which electrical output voltage of the instrument of FIG. 2 is plotted against the product of viscosity and fluid density, FIG. 4 being an enlarged version of a portion of the graph of FIG. 3.
Figure 4:
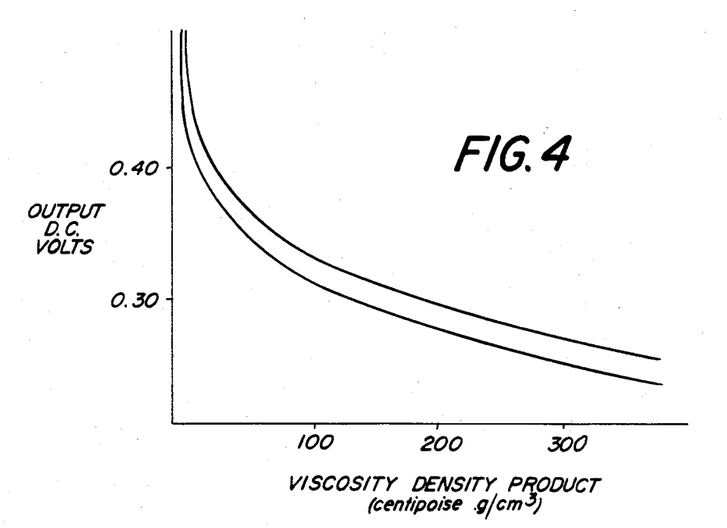

Node 34 is also connected through capacitor 36 and resistor 38 to one of the inputs of a second current mode differencing input amplifier 40 (also one-half of an LM359 amplifier). The output of amplifier 40 is connected through capacitor 42 and resistor 44, and through diode 46 to ground. A DC signal produced at the junction of resistor 44 and diode 46 is connected through resistor 48 to an input of digital voltmeter 52, there being a smoothing capacitor 50 connected between the input of the meter and ground. Digital voltmeter 52 is responsive to the voltage across the transducer. The voltage is dependent on the current in the transducer, which is indicative of the impedance of the mechanical system comprising transducer 17, the coupling layer (i.e. polyester sheet 14 and the adhesive securing the transducer to it), and the fluid sample. The reading provided by the digital voltmeter can be readily translated to the product of the density and viscosity of the fluid sample, as shown by the curves of FIGS. 3 and 4. Assuming that the density of the sample is known, the viscosity can be determined very simply. If desired, the signal delivered to the digital voltmeter can be translated directly into a viscosity reading by means of an analog-to-digital converter and computer, or through any of several other well-known techniques.

As stated previously, the function of sheet 14 is to couple the transducer to the fluid sample in such a way as to achieve optimum sensitivity. That is, to cause small differences in fluid sample viscosity to produce large differences in the readout of the digital voltmeter at least over the viscosity range of interest. The use of the coupling layer 14, by greatly improving the sensitivity of the instrument, makes it possible to achieve accurate and reliable viscosity readings by means of very simple mechanical apparatus, and very simple electronic circuitry. The manner in which these objectives are achieved by the use of the coupling layer is explained below.

To achieve optimum sensitivity, the coupling layer is selected to produce a substantially zero total reflection coefficient at a viscosity preferably at least approximately one-fiftieth the viscosity of the sample being measured.

The instrument achieves a substantially zero total reflection coefficient by relying on shear wave interference effects in the coupling layer. The thickness of the coupling layer is chosen so that constructive interference occurs in the shear wave transmitted into the fluid sample, while destructive interference cancels the shear wave reflected back into the transducer.

In general, the total reflection coefficient R in a system comprising a transducer, a coupling layer, and a viscoelastic fluid sample can be expressed as follows:

$$R = r_1 + \frac{a^2(1 - r_1^2)r_2 e^{i(\phi + \theta_2)}}{1 + a^2 r_1 r_2 e^{i(\phi + \theta_2)}} \quad (1)$$

where
  $r_1$ is the magnitude of the reflection coefficient at the interface between the transducer and the coupling layer and corresponds to $$r_1 = \frac{Z_1 - Z_2}{Z_1 + Z_2}$$

$Z_1$ is the acoustic impedance of the transducer;
$Z_2$ is the acoustic impedance of the coupling layer;
$r_2$ is the magnitude of the reflection coefficient at the interface between the coupling layer and the viscoelastic fluid and corresponds to $$r_2 = \frac{Z_2 - Z_3}{Z_2 + Z_3}$$

$Z_3$ is the acoustic impedance of the viscoelastic fluid;
a is the attenuation coefficient of the shear wave through the coupling layer;
$\phi$ is the phase shift due to the path length of the wave in the coupling layer (one round trip); and
$\theta_2$ is the phase shift at the interface between the coupling layer and the viscoelastic fluid.

The phase shift at the interface between the transducer and the coupling layer is assumed to be 0 for a wave entering the coupling layer and $\pi$ for a wave returning to the transducer.

If the thickness of the coupling layer is properly chosen, there is one particular fluid of viscosity $\eta_m$, which when placed on the coupling layer, causes the shear wave reflected back into the transducer to be zero. This fluid can be referred to as a "matching fluid", and its viscosity can be determined by setting the reflection coefficient R to equal zero.

The thickness of the coupling layer is preferably chosen so that $\phi$, the phase shift due to the path length, exactly cancels $\theta_2$, the phase shift at the coupling layer fluid interface when the fluid is the matching fluid. Then $\phi + \theta_2 = \pi$ and Therefore, equation (1) can be simplified to $$R = r_1 - \frac{a^2 r_2 (1 - r_1^2)}{1 - a^2 r_1 r_2} \quad (2)$$

If R is set to equal zero, we have $$r_1 = \frac{a^2 r_2 (1 - r_1^2)}{1 - a^2 r_1 r_2} \quad (3)$$

multiplying by the denominator:

$$r_1(1 - a^2 r_1 r_2) = a^2 r_2 (1 - r_1^2) \quad (4)$$

expanding:

$$r_1 - a^2 r_1^2 r_2 = a^2 r_2 - a^2 r_1^2 r_2 \quad (5)$$

eliminating matching terms:

$$r_1 = a^2 r_2 \quad (6)$$

Given that:
f is the frequency of the shear stress in coupling layer ($\omega = 2\pi f$);
$\rho$ is the density of the coupling layer;
$U_s$ is the shear wave velocity in the coupling layer;
$\alpha$ is the attenuation coefficient per unit of thickness of the coupling layer; and $Z_t$ is the shear impedance of the transducer, the thickness t of the coupling layer, the viscosity $\eta_m$ of the matching fluid can be calculated as follows.

The shear impedance of the coupling layer, which is a polymer and therefore a viscoelastic medium, has both a loss modulus and a storage modulus. Therefore, the shear impedance $Z_p$ can be expressed as:

$$Z_p = R_p + iX_p. \quad (7)$$

For shear waves in a viscoelastic medium, the loss modulus $R_p$ can be expressed as:

$$R_p = \frac{\rho}{\frac{1}{U_s} + \frac{\alpha^2 U_s}{\omega^2}} \quad (8)$$

The storage modulus can be expressed as:

$$X_p = \frac{\rho}{\frac{\alpha}{\omega} + \frac{\omega}{\alpha U_s^2}} \quad (9)$$

The next step is to determine the shear impedance of the matching fluid. This is accomplished by observing that the reflection coefficient $R_2$, at the interface between a polymeric coupling layer having a shear impedance $Z_p$ and a Newtonian fluid having a shear impedance $Z_1$ can be expressed as:

$$R_2 = \frac{Z_p - Z_1}{Z_p + Z_1} \quad (10)$$

The impedance of a viscoelastic fluid is given in general by the equation:

$$Z = \pm \left[ (i\omega\rho)\left(\eta + \frac{G}{i\omega}\right) \right]^{\frac{1}{2}} \quad (11)$$

where G is the modulus of elasticity, and $\eta$ is the viscosity.

If the fluid is inelastic, G=0 and $$Z = \sqrt{i\rho\omega\eta} \quad (12)$$

Since $\omega = 2\pi f$, $$Z = \sqrt{i 2\pi f \rho \eta} \quad \text{or} \quad (13)$$

$$Z = \sqrt{i} \cdot \sqrt{2} \cdot \sqrt{\pi f \rho \eta} \quad (14)$$

but $$\sqrt{i} = \frac{1 + i}{\sqrt{2}}.$$

Therefore, $$Z = (1 + i)\sqrt{\pi f \rho \eta} \quad (15)$$

If $\sqrt{\pi f \rho \eta}$ is defined as L, then $Z_1$ is $L(1+i)$.
Expanding equation (10) by equating $Z_1$ to $L(1+i)$:

$$R_2 = \frac{R_p + iX_p - L(1+i)}{R_p + iX_p + L(1+i)} \tag{16}$$

Rearranging equation (16):

$$R_2 = \frac{(R_p - L) + i(X_p - L)}{(R_p + L) + i(X_p + L)} \tag{17}$$

The magnitude of the reflection coefficient $R_2$ is:

$$|R_2| = \sqrt{R_2^* \cdot R_2} \tag{18}$$

$$|R_2| = \left( \frac{(R_p - L) - i(X_p - L)}{(R_p + L) - i(X_p + L)} \cdot \frac{(R_p - L) + i(X_p - L)}{(R_p + L) + i(X_p + L)} \right)^{\frac{1}{2}} \tag{19}$$

$$|R_2| = \left( \frac{2L + R_p + X_p - 2L(R_p + X_p)}{2L + R_p + X_p + 2L(R_p + X_p)} \right)^{\frac{1}{2}} \tag{20}$$

To determine the shear impedance of the matching fluid $R_2$ is set to equal $r_1/a^2$ in accordance with equation (6). The value of a, the attenuation coefficient in the coupling layer, is approximated by assuming that the required thickness is close to $\frac{1}{4}\lambda$ and determining the attenuation by multiplying the assumed thickness by $\alpha$, the attenuation coefficient per unit thickness. Then equation (20) is solved for L as follows:
Squaring both sides of (20):

$$r_2^2 = \frac{2L^2 + R_p^2 + X_p^2 - 2L(R_p + X_p)}{2L^2 + R_p^2 + X_p^2 + 2L(R_p + X_p)} \tag{21}$$

Multiplying by the denominator and then subtracting the numerator:

$$2L^2 r_2^2 + R_p^2 r_2^2 + X_p^2 r_2^2 + 2Lr_2^2(R_p+X_p) - 2L^2 - R_p^2 - X_p^2 + 2L(R_p+X_p) = 0 \tag{22}$$

This is a quadratic equation which can be solved for L in the usual manner. Thus, if $r_1$, the reflection coefficient at the interface between the transducer and coupling layer is determined from the shear impedance of the transducer $Z_t$ and the shear impedance of the coupling layer $Z_p$ (equations 7, 8 and 9) as follows:

$$r_1 = \frac{Z_t - Z_p}{Z_t + Z_p}, \tag{23}$$

and $r_2$ is set to equal $r_1/a^2$, the shear impedance $L_m$ of the matching fluid can be determined from equation (22).

As stated previously, the thickness of the coupling layer is chosen so that $\phi$, the phase shift due to the path length, exactly cancels $\theta_2$, the phase shaft at the coupling layer fluid interface when the fluid is the matching fluid. Thus:

$$\phi + \theta_2 = \pi; \tag{24}$$

or $$\phi = \pi - \theta_2 \tag{25}$$

The phase shift $\phi$ due to the path length is by definition:

$$\phi = \frac{2\pi(2t)}{\lambda} \tag{26}$$

where:
t is the thickness of the coupling layer; and
$\lambda$ is the wavelength in the coupling layer.
Substituting $\pi - \theta_2$ for $\phi$ and solving equation (26) for t:

$$\pi - \theta_2 = \frac{4\pi t}{\lambda} \tag{27}$$

$$t = \frac{\lambda(\pi - \theta_2)}{4\pi} \tag{28}$$

The phase shift $\theta_2$ can be calculated as follows from equation (17):

$$R_2 = \frac{(R_p - L) + i(X_p - L)}{(R_p + L) + i(X_p + L)} \tag{17}$$

Multiplying both numerator and denominator by the complex conjugate of the denominator to separate the real and imaginary components of $R_2$:

$$R_2 = \frac{(R_p - L) + i(X_p - L)}{(R_p + L) + i(X_p + L)} \cdot \frac{(R_p + L) - i(X_p + L)}{(R_p + L) - i(X_p + L)} \tag{29}$$

$$R_2 = \frac{R_p^2 + X_p^2 - 2L^2 + i(2LX_p - 2LR_p)}{(R_p + L)^2 + (X_p + L)^2} \tag{30}$$

$$\theta = \tan^{-1} \frac{2LX_p - 2LR_p}{R_p^2 + X_p^2 - 2L^2} \tag{31}$$

If $L_m$, the shear impedance of the matching fluid, as determined for equation (17) is substituted for L into equation (31), the value of $\theta_m$ can be determined and the thickness t of the coupling layer can be determined using equation (28) as follows:

$$t = \frac{\lambda(\pi - \theta_m)}{4\pi} \tag{32}$$

The viscosity $\eta_m$ of the matching fluid is determined from $L = \pi \rho \eta f$ as follows:

$$\eta_m = \frac{L_m^2}{\pi \rho f} \tag{33}$$

For any given transducer and coupling layer material, there is an optimum thickness. There is also a fluid viscosity (matching viscosity) for which the total reflection coefficient is zero. The optimum thickness and the matching viscosity can be determined in accordance with the following example.

Assume that the transducer has a shear impedance $Z_t$ of $1.27 \times 10^7$ Kg/m$^2$ sec; that the imaginary component $X_p$ of the acoustic shear impedance of the coupling layer is negligible compared to the real component $R_p$, and that $R_p$ is $1.13 \times 10^6$ Kg/m² sec. Further assume a velocity of shear waves in the coupling layer of 887.5 m/sec., an operating frequency of 1.98 MHz., and a shear wave attenuation of 34 db/cm.

The reflection coefficient $r_1$ at the interface of the transducer and coupling layer from equation (23) is:

$$\frac{Z_t - Z_p}{Z_t + Z_p}$$

Since $Z_p \approx R_p$, $$r_1 = \frac{Z_t - R_p}{Z_t + R_p} = \frac{12.7 - 1.3}{12.7 + 1.3} = 0.8143$$

The attenuation coefficient, a, cannot be precisely determined because the thickness of the coupling layer is not yet known. However, the attenuation coefficient can be approximated by assuming that the required thickness will be close to a quarter wavelength.

A quarter wavelength $\lambda/4$ is equal to $$\frac{U_s}{4f} = \frac{887.5}{4 \times 1.98 \times 10^6} = 1.12 \times 10^{-4}$$

Multiplying $\lambda/4$ by $\alpha$ we get $$\frac{\lambda}{4} \alpha = 1.12 \times 10^{-4} \times 3400 \frac{db}{m} = 0.38 \, db$$

As a ratio of initial to final amplitudes, a is:

$$a = \frac{1}{\log^{-1}\left(\frac{0.38}{20}\right)} = 0.95$$

From equation (6) $r_1 = a^2 r_2$.
Therefore $$r_2 = \frac{0.8143}{(0.95)^2} = 0.90$$

The matching fluid impedance $L_m$ can be determined from $r_2$ and $R_p$ from equation (22), simplified by assuming $X_p$ is zero:

$$2L_m^2 r_2^2 + r_p^2 r_2^2 + 2L_m r_2^2 - 2L_m^2 - r_p^2 + 2L_m R_p = 0 \quad (34)$$

rearranging and gathering terms:

$$(2r_2^2 - 2)L_m^2 + (2r_2^2 + 2R_p)L_m + (R_p^2 r_2^2 - R_p^2) = 0 \quad (35)$$

let $$a = 2r_2^2 - 2 = -0.38$$

$$b = 2r_2^2 + 2R_p = 2.26 \times 10^6$$

$$c = R_p^2 r_2^2 - R_p^2 = -2.4 \times 10^{11}$$

$$L_m = \frac{-b \pm \sqrt{b^2 - 4ac}}{2a}$$

$$L_m = 1.05 \times 10^5 \text{ or } 5.84 \times 10^6$$

The system will match impedances of either of these two values, but the higher number represents a material of higher shear impedance than that of the coupling layer. The instrument will never encounter a fluid have such a high impedance.

Choosing the value $1.05 \times 10^5$, the phase shift $\theta_2$ at the interface of the coupling layer and the matching fluid can be determined from equation (31) (ignoring $X_p$):

$$\theta_2 = \tan^{-1}\left(\frac{-2L_m R_p}{R_p^2 - 2L_m^2}\right)$$

$$\theta_2 = -10.7° \text{ or } -0.19 \text{ radians}$$

The thickness t of the coupling layer can now be determined from equation (28):

$$t = \frac{\lambda(\pi - \theta_2)}{4\pi} \quad (28)$$

Since $\lambda = U_s/f$, $$t = \frac{U_s(\pi - \theta_2)}{4\pi f} \quad (36)$$

$$t = \frac{887.5 (\pi + 0.19)}{4 \cdot \pi \cdot 1.98 \times 10^6}$$

$$t = 1.19 \times 10^{-4} \text{ m}$$

or .0047 inch.

The matching viscosity $\eta_m$ can be determined from equation (33):

$$\eta_m = \frac{L_m^2}{\pi \rho f} \quad (33)$$

$$\eta_m = \frac{1772}{\rho}$$

where $\rho$ is the density of the fluid.

Therefore, when the viscosity density product is 1772, the total reflection coefficient will be zero and the instrument will be most sensitive to variations in viscosity of the sample being measured.

From the above calculations, it will be noted that the coupling layer 0.0047 inch is seven percent thicker than one quarter wavelength (0.0044 inch). At the matching viscosity, the total reflection coefficient is zero, whereas with a one quarter wavelength coupling layer, the total reflection coefficient at the matching viscosity would be approximately 0.45. The advantage of the 0.0047 inch coupling layer over a quarter wavelength coupling layer is that sensitivity (i.e. the rate of change of the reflector coefficient with respect to viscosity) is improved over a wide range of viscosities, that is from 700 cp.$\times$g/cm³ up to the maximum viscosity that would ever be encountered. Thus a coupling layer designed in accordance with the invention can provide improved performance in a general purpose viscosity measuring instrument.

Much thicker coupling layers can be used, the thicknesses being based on multiples of quarter wavelengths adjusted to take the phase shift $\theta_2$ into account. However, these greater thicknesses would have unnecessary losses which would interfere with sensitivity. Therefore, as a practical matter the thickness of the coupling layer should always be slightly greater than one quarter wavelength but much less than one-half wavelength.

The curves in FIGS. 3 and 4 show the readings of voltmeter 52 over a viscosity density product range from about 10 to 5000 cp.×g/cm$^3$. The slope of the curves indicates a high degree of sensitivity throughout most of this range.

Temperature has an effect on the readings produced by the instrument as shown by the curves. The upper curve corresponds to a temperature of 20° C., while the lower curve corresponds to a temperature of 25° C. The curves are offset from each other by an approximately constant voltage. Therefore, if desired, a temperature compensating offset voltage can be introduced. Otherwise, the temperature of the sample should be controlled.

To optimize the instrument for a given viscosity range, the coupling layer material should be selected so that the matching viscosity falls approximately in the middle of the range. Thus, where the range of viscosities to be measured is high, a coupling layer material with a relative high shear impedance should be chosen. When the range of viscosities is low, a coupling layer with a relatively low shear impedance is preferable. In addition, the excitation frequency can be varied to select an appropriate matching viscosity $\eta_m$. In any case, the thickness of the coupling layer should be selected so that the total reflection coefficient comes as close as possible to zero at some viscosity, preferably at a viscosity near the middle of the range of interest.

In summary, using the foregoing procedure, if f, $\rho$, $U_s$, $\alpha$ and $Z_t$ are known, a coupling layer thickness can be determined which will produce a substantially zero total reflection coefficient at one particular value of sample viscosity. That particular viscosity value can also be determined.

The viscometer will have an optimum sensitivity at the viscosity for which the reflection coefficient is substantially zero. The viscometer will also have a low total reflection coefficient, and therefore a high sensitivity over a wide range of viscosities on both sides of the particular viscosity value for which the reflection coefficient is substantially zero.

If the viscosity corresponding to zero total reflection is in around 2000 centipoise, the instrument is useful as a practical matter over the entire range of viscosities which will normally be encountered. The instrument is highly sensitive even at viscosities fifty times the viscosity for which the total reflection is substantially zero.

The instrument of the invention can be modified in many ways. For example, if the shear transducer is a cadmium sulfide or zinc oxide transducer, it would be possible to manufacture the entire sensor by vacuum depositing both the transducer and the coupling layer onto a substrate. This would greatly simplify assembly. It may also be possible to make the sensor and associated electronics parts of a single integrated circuit where extreme miniaturization is desired. Shear rate can be varied by providing for variation in the amplitude of the signal applied to the transducer. Numerous other modifications in the materials, circuitry and mechanical configuration of the sensor can be made without departing from the scope of the invention as defined in the following claims.

I claim:

1. Apparatus for determining the viscosity of a fluid sample comprising:

an electromechanical transducer having a face capable of vibrating in shear mode when excited by an alternating electrical current;

electrical current generating means connected to said transducer for applying an alternating electrical current of predetermined frequency to the transducer and thereby exciting the transducer into shear vibration;

a solid coupling layer of substantially uniform thickness having one face in contact with said face of the transducer and having its opposite face free to come into contact with a fluid sample; and means, connected to the current generating means, for measuring the magnitude of the impedance of the system consisting of the transducer, coupling layer and fluid sample as presented to the generator;

wherein the thickness and shear impedance of the coupling layer are chosen so that, at least at one viscosity of a fluid sample in contact with said opposite face of the coupling layer, and at the frequency of said alternating electrical current, the magnitude of the shear wave reflected into the transducer through the interface between the coupling layer and the transducer is substantially zero.

2. Apparatus according to claim 1 in which the transducer is a piezoelectric transducer, and in which the measuring means is responsive to the electrical current in the transducer.

3. Apparatus according to claim 1 comprising a tubular support in which the coupling layer comprises a polymeric sheet placed over one end of the tubular support and secured to the edge thereof, and in which the transducer is adhesively secured to one face of the polymeric sheet and supported thereby.

4. Apparatus according to claim 1 in which the thickness of the coupling layer is greater than one-quarter wavelength but much less than a half wavelength at the frequency of the alternating electrical current and at the velocity of shear waves produced in the coupling layer at said frequency.

5. Apparatus according to claim 1 in which the coupling layer comprises a polyester sheet approximately 0.004 inch thick and an adhesive layer approximately 0.0007 inch thick connecting the polyester sheet to the transducer, and in which the frequency of the current produced by the generator is approximately 1.98 MHz.

6. A method of determining the viscosity of a fluid sample comprising the steps of:

causing the fluid sample to be situated in contact with one face of a coupling layer of solid sheet material, the other face of which is in contact with a face of an electromechanical shear transducer;

exciting the shear transducer into vibration by applying an alternating electrical current to it by means of an electrical current generator; and measuring the magnitude of the impedance of the system consisting of the transducer, coupling layer and fluid sample as presented to the generator;

wherein the thickness and shear impedance of the coupling layer are chosen so that, at least at one viscosity of a fluid sample situated in contact with said one face of the coupling layer, and at the frequency of the alternating current produced by the generator, the magnitude of the shear wave reflected into the transducer through the interface between the coupling layer and the transducer is substantially zero;

whereby the magnitude of said impedance is a measure of the viscosity of the fluid sample and whereby a high degree of sensitivity to variations in viscosity is achieved.

7. The method according to claim 6 in which the shear impedance and thickness of the coupling layer are chosen so that for at least one viscosity at least one-fiftieth of the the viscosity of the fluid sample, and at the frequency of the alternating current produced by the generator, the magnitude of the shear wave reflected into the transducer through the interface between the coupling layer and the transducer is substantially zero.

8. The method according to claim 6 in which the magnitude of the impedance of said system is measured by measuring the electrical current in the transducer.

* * * * *

UNITED STATES PATENT AND TRADEMARK OFFICE
CERTIFICATE OF CORRECTION

PATENT NO. : 4,721,874

DATED : January 26, 1988

INVENTOR(S) : Sans W. Emmert

It is certified that error appears in the above-identified patent and that said Letters Patent are hereby corrected as shown below:

Column 2, lines 61-62, "instrumennt" should be --instrument--;

Column 7, line 46, the hyphen at the end of the line should read --$p^2$--;

Column 7, line 47, delete "$p^2$";

Column 10, line 25, the second "=" should be "-"; and

Column 10, line 66 "$\theta^2$" should be --$\theta_2$--.

Signed and Sealed this

Twenty-fourth Day of May, 1988

*Attest:*

DONALD J. QUIGG

*Attesting Officer*   *Commissioner of Patents and Trademarks*